(12) United States Patent
Foti

(10) Patent No.: US 6,375,724 B1
(45) Date of Patent: *Apr. 23, 2002

(54) HUMIDIFILTER

(76) Inventor: James Kahekili Foti, 1343 Mokulua Dr., Kailua, HI (US) 96734

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/762,099

(22) Filed: May 13, 1997

(51) Int. Cl.[7] .................. A62B 7/00; A61M 15/00
(52) U.S. Cl. ............. 96/294; 55/522; 55/DIG. 35; 95/214; 96/240; 96/298; 128/203.29; 128/204.13; 128/204.14
(58) Field of Search .............. 55/522, DIG. 35; 96/294, 298, 240; 95/214, 281; 128/203.16, 203.29, 204.13, 204.14

(56) References Cited

U.S. PATENT DOCUMENTS

| 217,691 | A | * | 7/1879 | Hurd | 128/203.29 |
| 2,228,502 | A | * | 1/1941 | Boothby | 128/201.19 |
| 3,612,049 | A | * | 10/1971 | Monson | 128/203.29 |
| 3,873,281 | A | * | 3/1975 | Himes et al. | 55/522 |
| 3,881,482 | A | * | 5/1975 | Lindholm | 128/204.13 |
| 3,980,080 | A | * | 9/1976 | Muto | 55/DIG. 35 |
| 4,146,026 | A | * | 3/1979 | Montalvo | 128/206.12 |
| 4,267,831 | A | * | 5/1981 | Aguilar | 128/203.14 |
| 4,304,230 | A | * | 12/1981 | Seufert | 55/DIG. 35 |
| 4,503,851 | A | * | 3/1985 | Braunroth | 128/203.29 |
| 4,705,033 | A | * | 11/1987 | Halfpenny | 128/201.13 |
| 4,941,467 | A | * | 7/1990 | Tarata | 128/203.29 |
| 4,964,900 | A | * | 10/1990 | Thompson et al. | 55/DIG. 35 |

* cited by examiner

Primary Examiner—Duane Smith
Assistant Examiner—Minh-Chau T. Pham
(74) Attorney, Agent, or Firm—Robert M Hunter

(57) ABSTRACT

The invention is a humidification and filtration mask having an open cell foam reservoir attached to the facial or inner surface of a paper filtration mask. The reservoir provides for evenly wetting the paper mask by capillary action, after being charged with water. The device offers low inspiratory airway resistance compared to other art and is lighter and less costly.

20 Claims, 1 Drawing Sheet

HUMIDIFILTER

CROSS-REFERENCES TO RELATED APPLICATIONS

| b) CROSS REFERENCES TO RELATED APPLICATIONS | | | |
|---|---|---|---|
| 3,612,049 | 10/71 | Monson | 128/203.29 |
| 3,881,482 | 05/75 | Lindholm | 128/204.13 |
| 4,267,831 | 05/81 | Aguilar | 128/204.14 |
| 4,146,026 | 03/79 | Montalvo | 128/206.12 |
| 4,705,033 | 11/87 | Halfpenny | 128/201.13 |
| 4,941,467 | 07/90 | Takata | 128/203.29 |
| 4,503,851 | 03/85 | Braunroth | 128/203.29 |

STATEMENT REGARDING FEDERALLY SPONSORED RESEARCH OR DEVELOPMENT

NONE (NOT APPLICABLE)

REFERENCE TO MICROFICHE APPENDIX

NONE (NOT APPLICABLE)

BACKGROUND OF INVENTION

1) Technical Field

The invention falls within the field of protective filtration masks. In particular, it is adapted to easily provide humidification as well as filtration of inspired air in conditions where ambient air is excessively dry. It has particularly been designed to serve the needs of patients with chronic lung disorders.

2) Background Art

A number of similar devices have been patented for this same purpose since 1897. Humidification and filtration of ambient air which is low in humidity and high in particulate matter and microbes is not a new concept: benefits are cited in a number of the patent documents, particularly in U.S. Pat. No. 3,612,049, "personal humidifier", by A. V. Monson, U.S. Pat. No. 3,881,482, "device for moistening and heating inhalation air with tracheostomy and endotracheal tube intubation" by C. Lindholm, U.S. Pat. No. 4,267,831, "nasal air filter and medicament device" by M. Aguilar, and U.S. Pat. No. 4,146,026, "filter mask", by V. H. Montalvo.

Particularly similarly conceived devices were patented since 1987: U.S. Pat. No. 4,705,033, "humidification face mask" by P. F. Halfpenny, U.S. Pat. No. 4,941,467, "humidification face mask", by D. Takata, and U.S. Pat. No. 4,503,851 by K. Braunroth.

The heretofore patented devices provide both filtration and humidification of dry ambient air. They also result in relatively and significantly increased inspiratory air flow resistance. They are heavier and therefore less comfortable to wear. Cost and ease of distribution to large groups (e.g. air travelers) is an obstacle to accessibility.

It is specifically the object of the invention to provide an easily affordable, disposable humidifying and filtering mask, useful for persons with normal lungs, but particularly adaptable to individuals with chronic lung disease who can not generate sufficient negative inspiratory force to make use of existing masks realistic.

Chronic lung disorders are extremely common and more severe in older people in general. Individuals with such conditions are subject to exacerbations due to exposure to pulmonary irritants, microbes, and excessively dry air, all of which are encountered in long distance air craft travel and similar environments. These lung disorders are most often associated with impaired lung function. Individuals with these disorders benefit most from humidification and filtration. A significant deterrent to prolonged use of these devices is that resistance to inspiration and its effect on the work of breathing imposed by the device mitigates against its comfortable and safe use.

The invention allows achievement of relatively comfortable humidification and filtration with imposition of the lowest inspiratory resistance of any practical personal device currently available because inspiration is accomplished through the entire porous surface of paper mask, as opposed to restricted orifice sizes.

BRIEF SUMMARY OF INVENTION

Humidifying filtration mask devised to provide lowest possible inspiratory air flow resistance by utilizing a paper filter mask provided with an open cell foam reservoir on its inner or facial surface; particularly suitable for use by individuals with chronic lung disorders and respiratory insufficiency.

DETAILED DESCRIPTION

Figure 1:
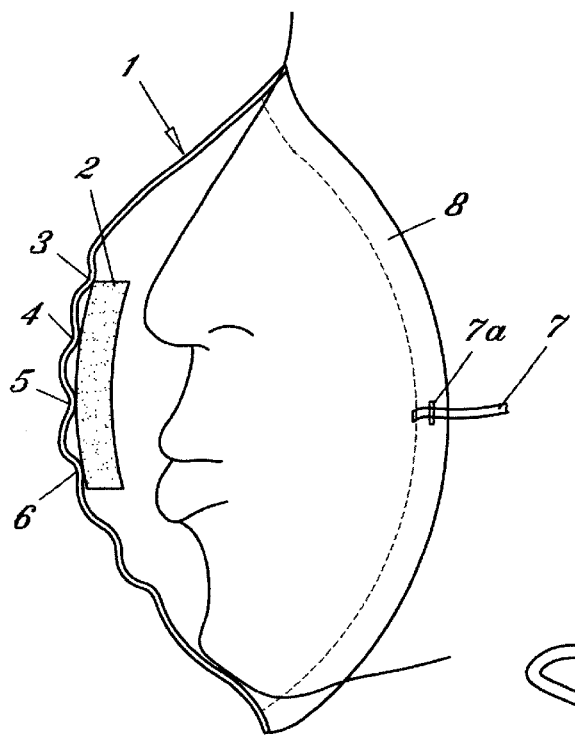
FIGS. 1, 2, & 3 respectively present perspectives, cutaway and sagittal sections, right sided oblique of the facial side, and of the back of the mask.

FIG. 1 depicts the mask over the face and held in place by rubber band 7 which is secured to the sided of the mask with stainless staples 7a. Paper mask 1 is shown with the commonly encountered corrugated snout, which helps to maintain concavity towards the face. The open cell foam reservoir 2 measures approximately 4×4×1 cm., and is secured to the mask by glue points, sutures, or plastic rivets at three or more points at levels 3, 4, 5, & 6. A coating or liner of plastic glaze 8 of a flexible nature is depicted along the facial edge of the mask to prevent irritation to the skin by long term exposure to the wet paper of the mask.

Figure 2:
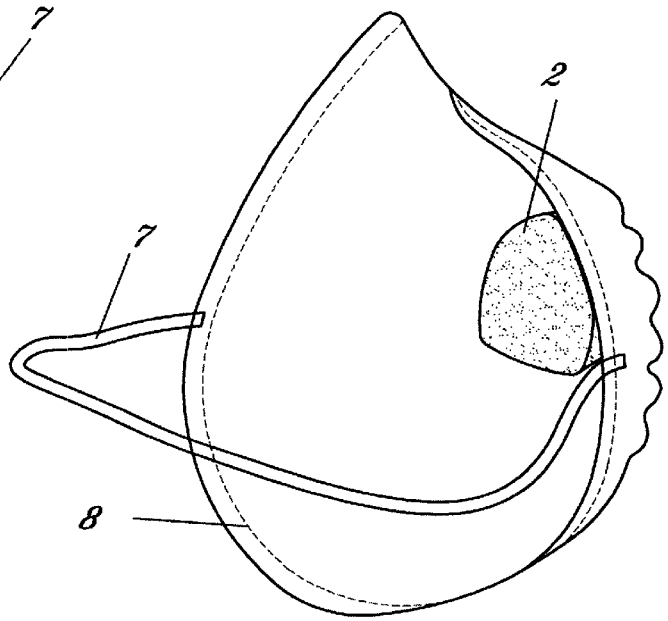

FIG. 2 depicts the placement position of the reservoir 2 in oblique view from the right, along with the elastic 7 and the plastic shield 8.

Figure 3:
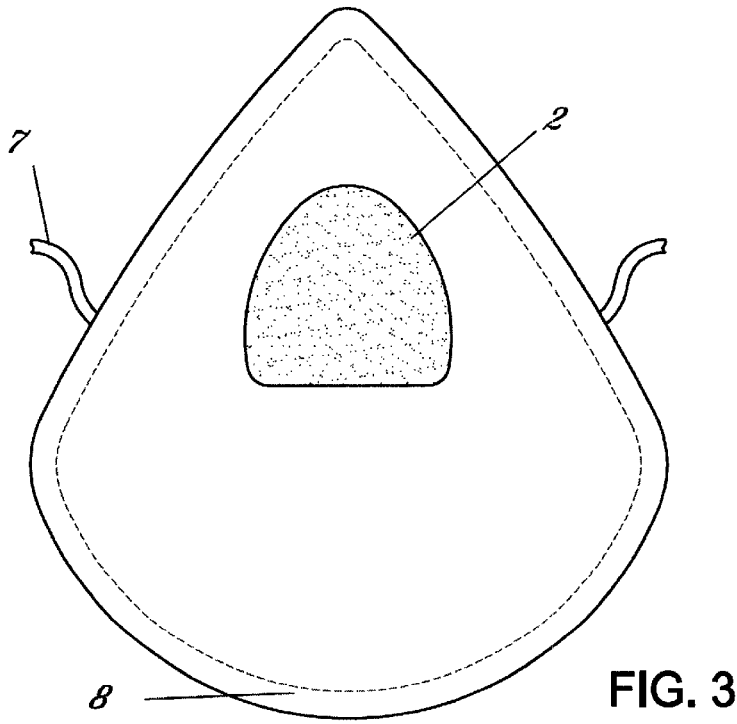

FIG. 3 depicts the reservoir approximate shape and location from the back of the mask 1, along with elastic band 7 and plastic liner 8.

Best Mode for Application

The mask can be mass produced at relatively low costs so that distribution to large numbers of individuals may be facilitated and made more accessible, particularly to individuals with chronic lung disorders. It may be used during most of the hours of closed doors and flight within aircraft. A teaspoon (5 mL) of water charges the reservoir 2 which disperses moisture evenly throughout the material of the paper mask 1. The negative inspiratory force required for inspiration through the complex is imperceptibly greater then normal inspiration without a mask. It is compatible with devices for administration of supplemental oxygen. Expired air is rich in moisture, and recharges the mask and reservoir without addition of more water, except under extreme conditions of dry ambient air.

What is claimed is:

1. A humidifying filtration mask comprising:
   a wettable paper mask, said paper mask having a porous surface, two sides, a facial edge and a corrugated snout having at least four levels or corrugations and an inner surface;

an elastic band having two ends, one end of which is attached to each side of said paper mask with a staple; and a water reservoir attached to said inner surface of said snout at three or more points along each level or corrugation with glue points, sutures or plastic rivets in such a way as to cause substantially even wetting of said mask by capillary action when water is added to said water reservoir;

wherein said mask is operative to allow inspiration by a wearer through the entire porous surface when said mask is so wetted.

2. The humidifying filtration mask of claim 1 wherein said water reservoir is composed of an open cell foam.

3. The humidifying filtration mask of claim 1 further comprising a flexible, waterproof coating applied along said facial edge, said coating being composed of a plastic glaze.

4. The humidifying filtration mask of claim 1 wherein said water reservoir has a water-holding capacity of at least five milliliters.

5. A humidifying filtration mask comprising:

a wettable paper mask, said paper mask having a porous surface, two sides, a facial edge and a snout having a plurality of levels or corrugations and an inner surface;

an elastic band having two ends, one end of which is attached to each side of said paper mask; and a water reservoir attached to said inner surface of said snout at a plurality of points along each level or corrugation in such a way as to cause substantially even wetting of said mask by capillary action when water is added to said reservoir.

6. The humidifying filtration mask of claim 5 wherein said mask is comprised of a filter paper cone.

7. The humidifying filtration mask of claim 5 wherein the elastic band is comprised of rubber.

8. The humidifying filtration mask of claim 5 further comprising a flexible, waterproof coating applied along said facial edge.

9. The humidifying filtration mask of claim 5 wherein the water reservoir is comprised of open cell foam.

10. The humidifying filtration mask of claim 5 wherein said snout has at least four levels or corrugations and said water reservoir is attached to said inner surface of said snout at three or more points along each level or corrugation.

11. The humidifying filtration mask of claim 5 wherein said water reservoir has a water-holding capacity of at least five milliliters.

12. The humidifying filtration mask of claim 5 wherein each of said ends is attached to a side of said paper mask by a stainless steel staple.

13. A humidifying filtration mask comprising:

a wettable porous mask, said mask having two sides, a facial edge and an inner surface;

an elastic band having two ends, one end of which is attached to each side of said mask;

an impermeable coating on said facial edge; and a reservoir attached to said inner surface of said mask at a plurality of points in a way that is operative to cause substantially even wetting of said mask by capillary action when water is added to said reservoir.

14. The humidifying filtration mask of claim 13 wherein said mask is comprised of paper.

15. The humidifying filtration mask of claim 13 wherein the elastic band is comprised of rubber.

16. The humidifying filtration mask of claim 13 wherein the impermeable coating comprises a plastic glaze.

17. The humidifying filtration mask of claim 13 wherein the reservoir is comprised of open cell foam.

18. The humidifying filtration mask of claim 13 wherein the reservoir has a water-holding capacity of at least five milliliters.

19. The humidifying filtration mask of claim 13 wherein each of said ends is attached to one side of said paper mask by a stainless steel staple.

20. The humidifying filtration mask of claim 13 wherein the impermeable coating is operative to prevent irritation of the skin of a user of the mask.

* * * * *

UNITED STATES PATENT AND TRADEMARK OFFICE
Certificate

Patent No. 6,375,724 B1                                                  Patented: April 23, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James Kahekili Foti, Kailua, HI; and Philip Robert Foti, Kailua, HI.

Signed and Sealed this Eighth Day of April 2003.

*TOM G. DUNN*
*Supervisory Patent Examiner*
*Art Unit 1724*